United States Patent [19]

Havener et al.

[11] Patent Number: 5,488,312

[45] Date of Patent: Jan. 30, 1996

[54] METER WITH PROBE FOR MEASURING THE MOISTURE CONTENT OF STACKED WOOD

[75] Inventors: Robert T. Havener, Grants Pass; Edward D. Wagner, Rogue River, both of Oreg.

[73] Assignee: Wagner Electronic Products, Inc., Rogue River, Oreg.

[21] Appl. No.: 348,457

[22] Filed: Dec. 2, 1994

Related U.S. Application Data

[62] Division of Ser. No. 992,733, Dec. 18, 1992, Pat. No. 5,402,076.

[51] Int. Cl.⁶ .................................................. G01R 27/26
[52] U.S. Cl. .................... 324/689; 324/690; 324/724; 414/789.5; 294/81.21; 294/81.54
[58] Field of Search .................... 73/886,5; 324/690, 324/687, 689; 414/789.5; 294/81.21, 81.54

[56] References Cited

U.S. PATENT DOCUMENTS 3,581,197   5/1971   Morey ..................................... 324/690

5,402,076   3/1995   Havener ................................... 324/689

*Primary Examiner*—Kenneth A. Wieder
*Assistant Examiner*—Jose M. Solis
*Attorney, Agent, or Firm*—Klarquist Sparkman Campbell Leigh & Whinston

[57] ABSTRACT

A meter for measuring the moisture content of wood in the center of a stack of wood has a probe with an electromagnetic wave sensor mounted near a forward end and a meter mounted at an opposite end. An extendable member is also mounted at the forward end of the probe. The extendable member is pivoted by a slide handle at the opposite end of the probe between reclined and extended positions. The forward end of the probe is inserted into a stack of wood between layers of the stack. The extendable member is extended to press the sensor against wood in the center of the stack. The meter then registers the moisture content of the wood.

19 Claims, 2 Drawing Sheets

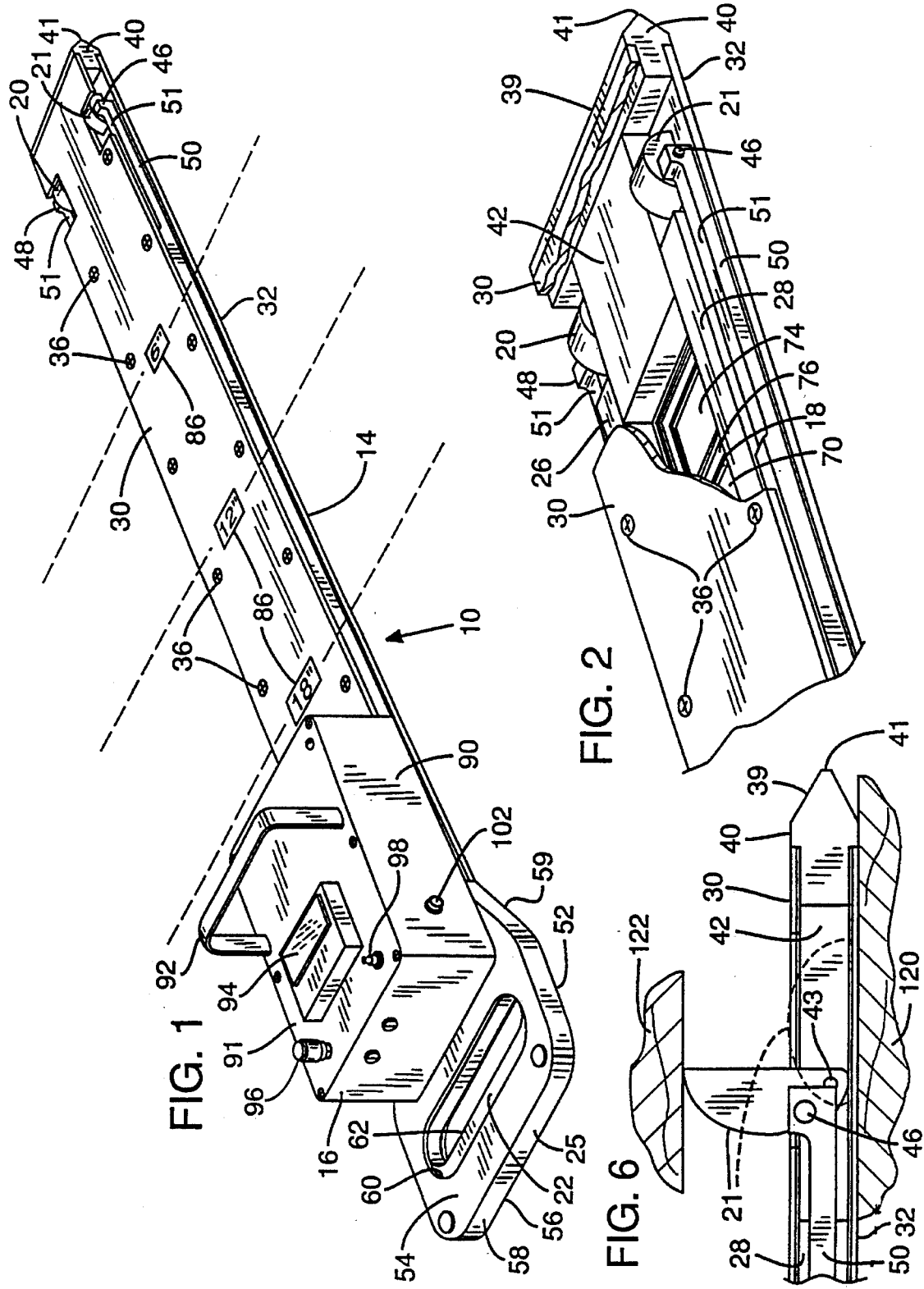

METER WITH PROBE FOR MEASURING THE MOISTURE CONTENT OF STACKED WOOD

This is a division of application Ser. No. 07/992,733, filed Dec. 18, 1992, now U.S. Pat. No. 5,402,076.

FIELD OF THE INVENTION

The present invention relates generally to moisture detection devices and, more particularly, relates to a device for detecting the moisture content of stacked wood using electromagnetic waves.

BACKGROUND OF THE INVENTION

After logs are milled to form lumber, the lumber is usually stacked for drying. Typically, the lumber is stacked in layers separated by transversely extending spacers called "stickers". For example, each layer of a stack may consist of two inch by four inch beams (two by fours) laid side by side lengthwise. Layers in a stack could also consist of beams of other dimensions, boards, planks, or the like. Between each layer, one inch by two inch or other dimensioned stickers are laid crosswise to the two by fours to allow air to circulate around and dry the two by fours. Often, the stacks are located in a kiln or drying oven to provide a controlled, heated environment for more rapid drying.

Usually, the lumber on the outer sides of a stack is subjected to a greater circulation of dry air than is the lumber in the stack's center, resulting in the lumber on the outer sides drying faster. Also, the lumber in the same layer of a stack may vary significantly in its initial moisture content. Therefore, estimating the dryness of the lumber in the stack's center by measuring the moisture content of the lumber on the outer sides of the stack is usually inaccurate. To better regulate the drying process, it is frequently desirable to determine the moisture content of the lumber in the center of a stack of wood without having to remove lumber from the stack.

One type of moisture detector used to measure the moisture content of wood uses two pin-shaped electrodes which are driven a predetermined distance apart into a piece of wood. With the electrodes inserted into a piece of wood, the moisture detector applies a voltage across the two electrodes and measures the current flowing between the electrodes. The amount of current flowing between the electrodes for a given voltage difference between the electrodes is directly related to the moisture content of the wood. Thus, by properly scaling the measured amount of current flow, the moisture detector is able to determine the moisture content of wood.

There are several problems with using this type of moisture detector to determine the moisture content of wood in the center of a stack of wood. First, it is difficult to drive pin-shaped electrodes into the wood in the stack's center. One apparatus which attempts to overcome this limitation comprises a rod with a T-shaped handle at one end. A flange is mounted at an end of the rod opposite the handle and projects perpendicularly to the rod. Two pin-shaped electrodes are mounted to project perpendicularly from the flange approximately one and a half inches from the rod. The electrodes are connected to wires which run through a hollow center of the rod to a co-axial cable connector attached to the handle. A meter which provides a voltage to the electrodes and measures the current flow connects to the electrodes using the coaxial cable connector.

The rod and flange act as a lever arm for driving the electrodes into a piece of wood in the center of a stack. First, the rod is inserted between layers of the stack with the flange oriented horizontally and the electrodes pointing upwards. With the electrodes pointing towards a piece of wood in the layer of the stack above the device, the rod is rotated about its longitudinal axis using the handle. During rotation, the rod seats against the layer of the stack beneath the apparatus and the flange rotates upward. This moves the electrodes on the flange towards the wood and drives them into the wood.

A second problem with moisture measurement devices employing pin-shaped electrodes is that because the electrodes are driven into the wood, the wood is damaged when its moisture content is measured. A further problem is that it is difficult to measure the moisture deep within a piece of wood. To measure the moisture deeply within the wood, considerable force must be used to drive the electrodes deeply into the wood, resulting in even greater damage to the wood.

A second type of device for measuring the moisture content of wood uses an electromagnetic wave detection technique. One such device is the prior art Hand-Held Moisture Meter Model L601 (the L601 Meter) manufactured by Wagner Electronic Products. The L601 meter has a sensor comprising three electrodes: a transmitting, a receiving, and a ground electrode. These electrodes are configured as flat conducting plates which are placed against or in close proximity to a piece of wood whose moisture content is to be measured.

The transmitting electrode is driven with a radio frequency (RF) excitation signal generated by an oscillator circuit to produce electromagnetic waves. When the electrodes are placed against or in close proximity to wood, the electromagnetic waves penetrate into the wood in a volume which is approximately 1 inch deep and 3 inches square. The electromagnetic waves induce an RF sensing signal in the receiving electrode whose amplitude is related to the moisture content of the wood. The L601 Meter displays the amplitude of the RF sensing signal on an analog display calibrated to show the moisture content of the wood.

The L601 Meter and like electromagnetic wave detection devices eliminate the need for driving pin-shaped electrodes into wood to measure its moisture content. However, such devices are only effective for measuring wood which is in close proximity to the sensor.

SUMMARY OF THE INVENTION

In accordance with the present invention, a device for detecting the moisture content of stacked wood using electromagnetic wave detection is provided. The device comprises an elongated probe, an electromagnetic wave sensor, a handle and a meter. The sensor is located near a forward end of the probe. The handle is provided at an opposite end of the probe. The meter is mounted to the probe near the handle. The sensor is connected to the meter with wires.

The probe is thin to fit between layers of stacked wood. By inserting the probe forward end first between stack layers, the sensor may be placed in close proximity to a piece of wood deep within the stack whose moisture content is to be measured. The probe can be maneuvered to place the sensor in the correct position between the layers by hand using the handle. In its correct position, the sensor, or the portion of the probe containing the sensor, should be pressed against the wood. When correctly positioned, the meter determines the moisture content of the wood using electromagnetic waves.

Because the layer of the stack containing the wood to be measured is uneven or for other reasons, it is at times difficult to properly position the sensor so that it is pressed against the wood. In accordance with a further aspect of the invention, to aid in properly positioning the sensor against the wood, the device may additionally comprise an extendable member at the forward end of the probe which can be remotely extended by the user who is holding the opposite or handle end of the device. The extendable member is located on a side of the probe opposite the sensor. For example, if the sensor is located on a bottom side of the probe, the extendable member is located on a top side of the probe.

Utilization of the extendable member is as follows. After inserting the probe between layers of a stack of wood with the sensor directly above the wood to be measured (assuming the configuration with the sensor on the bottom side of the probe), the extendable member is actuated. Actuation of the extendable member extends it upwards away from the top side of the probe. As it is extended, the extendable member pushes the probe away from the layer of the stack above the probe and towards the layer below the probe. The sensor is thereby pressed against the layer below the probe. By applying a force to position the sensor against the wood, the accuracy of the moisture content measurement is increased.

Additional features and advantages of the invention will be made apparent from the following detailed description of a preferred embodiment which proceeds with reference to the accompanying drawings.

BRIEF DESCRIPTION OF THE DRAWINGS

FIG. 1 is a perspective view of a device for measuring the moisture content of stacked wood in accordance with a first embodiment of the present invention;

FIG. 2 is a cut-away perspective view of a portion of the device shown in FIG. 1;

FIG. 6 is a side view of a portion of the device shown in FIG. 4.

DETAILED DESCRIPTION OF THE PREFERRED EMBODIMENTS

Figure 3:
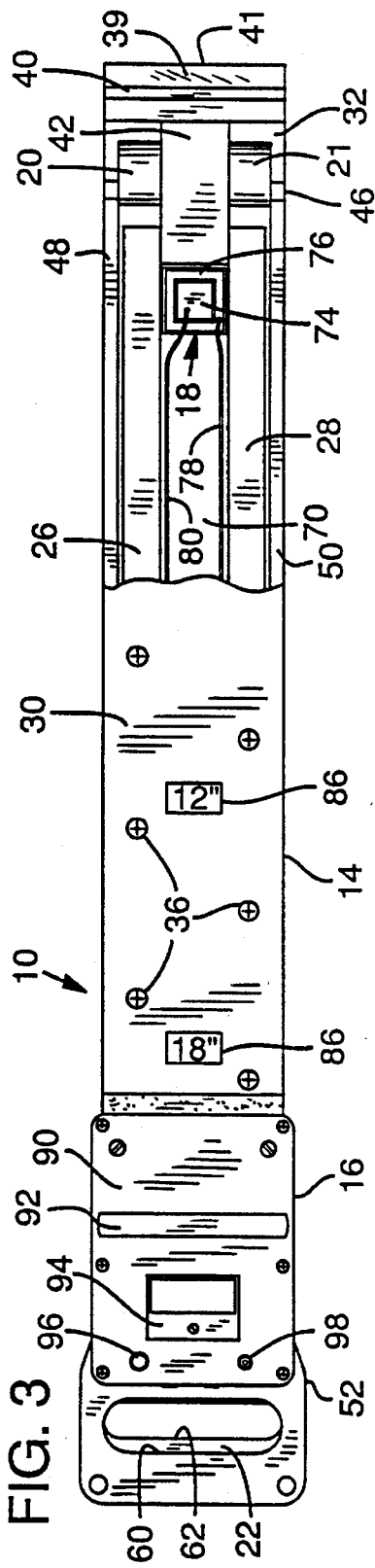
FIG. 3 is a cut-away top view of the device shown in FIG. 1.

With reference to FIG. 1, a device 10 for measuring the moisture content of wood according to a first embodiment of the present invention comprises a probe 14, a moisture content meter 16, an electromagnetic wave sensor 18 (shown in FIGS. 2 and 3), left and right cam levers 20, 21, and a slide handle 22. The illustrated probe 14 is a flattened, elongated member with the approximate dimensions of 34½ inches long by 5⅛ inches wide by ½ inch in height. Preferably the probe is thin enough to fit between layers of lumber separated by stickers. The sensor 18 is located within the probe near a bottom surface of the probe and approximately 4 inches from a forward end 24 of the probe. The cam levers 20, 21 are located on a top side of the probe, between the sensor 18 and the forward end 24 of the probe. The relative position of these elements can be varied, such as reversed. The meter 16 is mounted on the top side of the probe at an opposite end 25 of the probe. The slide handle 22 is also at the opposite end 25 of the probe.

As shown in FIGS. 2, 3, 5, and 6, the illustrated probe 14 comprises left and right longitudinal support members 26, 28, and top and bottom cover plates 30, 32. The support members 26, 28 are parallel to each other and separated by a distance of approximately 2 inches. The support members 26, 28 are sandwiched between the cover plates 30, 32. The support members 26, 28 and the cover plates 30, 32 define a longitudinal hollow cavity between the support members 26, 28. The hollow cavity begins at the opposite end 25 of the probe beneath the meter 16 and extends nearly to the forward end 24 of the probe. Each of the cover plates 30, 32 is constructed of fiberglass or other suitable material. One specific material is a fiberglass circuit board material with an underlying copper sheet for shielding purposes, with the shield being etched or otherwise separated to form RF electrodes 74, 76 for use as explained below. The cover plates 30, 32 are attached to the support members 26, 28 with screws 36. The heads of the screws 36 are flush with the outer surface of the cover plates 30, 32.

At the forward end 24, the probe 14 comprises a nose member 40 having a forward face 39 which tapers outwardly from the top and bottom to form a forward-projecting horizontal ridge 41 at the center of the forward face. The resulting wedge shape of the nose member 40 aids in guiding the insertion of the probe between the layers of lumber. The nose member 40 is attached to a forward end of a support block 42 which is approximately 2 inches in width. An opposite end of the support block fits between the support members 26, 28 at a forward extent of the hollow cavity in the probe 14. The nose member 40, support block 42, and support members 26, 28 are typically attached together, as with glue. Like the support members 26, 28, the nose member 40 and support block 42 are also sandwiched between the top and bottom cover plates.

The cam levers 20, 21 operate as extendable members for pressing the sensor against wood deep within a stack of wood. The cam levers 20, 21 are located between the support members 26, 28 and the nose member 40, one on each side of the support block 42. The top cover plate 30 is notched or indented at this location so that the cam levers 20, 21 remain uncovered, allowing the cam levers 20, 21 to be extended above the probe 14.

Each of the cam levers 20, 21 have a planar bottom surface and a curved top surface. The cam levers 20, 21 are pivotally mounted at a rearward end on a pin 43 (FIG. 6) which extends through the support block 42. The cam levers 20, 21 pivot on the pin between a reclined position in which their bottom surfaces are flush (see FIG. 2) against the bottom cover plate 32 and an extended position in which their bottom surfaces are vertical (see FIG. 6). When in the reclined position, the curved top surfaces of the cam levers 20, 21 are flush with the top cover plate 30. In their extended position, however, the cam levers 20, 21 project outwardly from the probe and above the top cover plate 30.

The cam levers 20, 21 are also rotatably attached by pins 46 extending from a top center position on the outer sides of the cam levers to left and right arms 48, 50. The arms 48, 50 are slidable and extend along the left and right sides of the probe between the cover plates 30, 32 and next to the support members 26, 28. The arms 48, 50 are an extension of the slide handle 22 at the opposite end 25 of the probe 14. When the arms 48, 50 are moved towards the opposite end 25 of the probe by sliding the slide handle 22, the cam levers 20, 21 are moved from their reclined to their extended position. The arms 48, 50 have recessed portions 51 on their top sides near their forward ends to prevent the arms from rubbing or binding against the top cover plate 30 and restricting the pivoting motion of the cam levers 20, 21 as the arms 48, 50 are slid to actuate the cam levers.

Referring now to FIGS. 1 and 3, at the opposite end 25 of the probe 14, a casing 52 for the slide handle 22 is attached to the probe. The casing 52 comprises a top 54, a bottom 56, and a side wall 58 which define a hollow cavity in which the slide handle 22 is encased. The top and bottom walls 54, 56 of the casing 52 are level with the top and bottom cover plates 30, 32 respectively. Thus, the casing 52 has the same height as the probe 14. However, the casing 52 is wider than the probe 14 and tapers at a forward end 59 where it attaches to the probe.

An oblong opening 60 is provided in the top and bottom walls 54, 56 transverse to the longitudinal axis of the probe 14 and approximately one inch from the opposite end 25 of the probe. The opening 60 is sized to permit insertion of a hand into the opening. Within the hollow of the casing 52 is the slide handle 22. The slide handle 22 is a solid member which fits snugly but slidingly within the casing. A second oblong opening 62 through the slide handle is provided and aligns with the opening 60 in the casing 52. The opening 62 is narrower in width than the opening 60. This permits a user to slide the slide handle 22 between a forward position in which the forward sides of the openings 60, 62 are aligned and a rearward position in which the rearward sides of the openings 60, 62 are aligned. Further, when the slide handle is slid to the forward position, the arms 48, 50 are pushed forward placing the cam levers 20, 21 in their reclined position. When the slide handle is slid towards its rearward position, the arms are retracted rearward moving the cam levers 20, 21 to their extended position.

Figure 5:
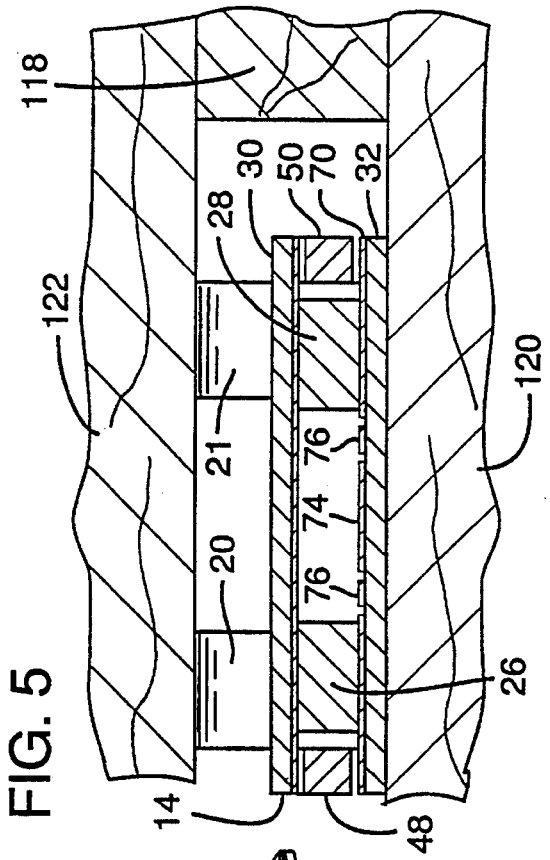
FIG. 5 is a sectional view of the device shown in FIG. 4 taken on line 5—5.

With reference to FIGS. 2, 3, and 5, the sensor 18 is provided on the bottom cover plate 32 within the hollow cavity of the probe. Although the sensor 18 may simply be mounted in the desired position, in the illustrated embodiment the sensor is formed from a portion of a conductive surface, such as copper, at an inside surface 70 of the bottom cover plate. More specifically, electrodes may be formed by etching the copper on the inside surface 70. In an illustrated form, the electrodes may comprise an inner square copper electrode 74 and an outer square annular electrode 76 surrounding and spaced from the inner electrode 74. The electrodes are connected to the meter 16 with wires 78, 80. The copper-plated inside surface 70 is also connected to a ground wire of the meter 16. The electrodes 74, 76 are driven by the meter 16 with an RF excitation signal to produce electromagnetic waves. An RF sensing signal will be induced in the electrodes 74, 76 dependent on the proximity of the electrodes to wood and on the moisture content of the wood.

Referring again to FIG. 1, the probe also comprises depth indicia 86 on an outer exposed surface of the probe, such as on the exposed surface of the top cover plate 30. The depth indicia 86 indicates the longitudinal distance along the probe from the center of the sensor 18 and may be used to determine how far the sensor has been inserted into a stack of wood. In the illustrated embodiment, the indicia consist of numerical labels placed at six inch intervals (namely, 6", 12" and 18") However, other suitable means such as solid lines drawn transversely across the probe at uniform intervals or a conventional ruler-type scale could be used.

Referring now to FIGS. 1 and 3, the meter 16 mounted on the top side of the probe comprises a box-shaped meter housing 90 having a lid 91 attached with screws. The housing 90 encases a rechargeable battery and circuitry for moisture detection using electromagnetic waves. To aid in handling the device 10, a U-shaped handle 92 is mounted transverse to the longitudinal axis of the probe on the lid 91. An analog needle and dial indicator 94 is also mounted on the lid 91. The indicator 94 has a scale which reads moisture content between 6 and 30 percent. The indicator 94 has a built-in electric bulb for illuminating the indicator when the device is used in dim light.

Also mounted on the lid 91 of the meter housing 90 are a calibration knob 96 and an actuation button 98. The actuation button turns on the meter 16 by providing power from the rechargeable battery to the circuitry encased in the housing. The circuitry includes an automatic shut-off feature to prevent unnecessary use of battery power. Thus, a needle in the indicator 94 registers the moisture content as measured by the sensor 18 after the actuation knob 98 is pressed. The calibration knob 96 is used to re-calibrate the meter 16 to compensate for battery drain and other variable conditions. A zero-adjust screw (not shown) used to zero the meter 16 is located inside the housing 90. The zero-adjust screw may be accessed through a hole (not shown) in a side of the housing 90. The hole is normally covered with a dust cap.

The rechargeable battery in the meter housing 90 can be recharged with a conventional charging unit which plugs into a 110 Volt, 60 Hz AC power outlet. A charging socket 102 is provided in a sidewall of the housing 90 for this purpose. The charging socket 102 receives a standard connector provided on conventional charging units.

One suitable meter 16 with the above described features is an L601 meter from Wagner Electronic Products of Rogue River, Oreg. Other RF signal generating/receiving and indicating devices may also be used.

Figure 4:
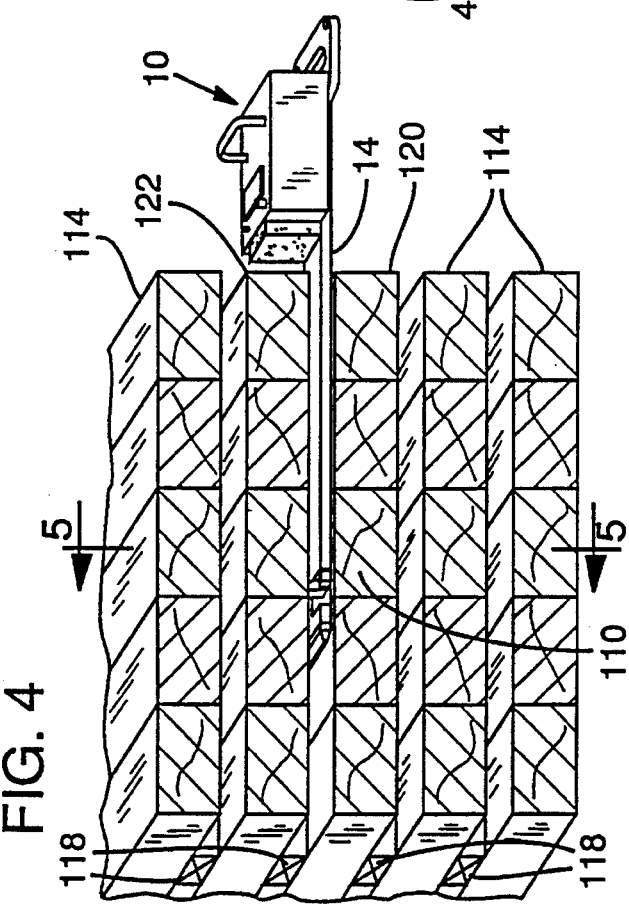
FIG. 4 is a side view of the device shown in FIG. 1 while in use measuring the moisture content of a piece of lumber within a stack of wood.

FIGS. 4–6 illustrates the device 10 being used to measure the moisture content of a piece of wood 110 in a stack of wood 112. The stack of wood 112 comprises a plurality of layers 114 of two by four beams laid side by side lengthwise. The layers 114 are separated by one inch by two inch stickers 118 which provide gaps of about ¾ to one inch in height between the layers.

Before the measurement is made, the meter 16 of the device 10 should be properly calibrated and zeroed using the calibration knob 96 and the zero adjust screw. To measure the moisture content of the piece of wood 110, the probe 14 of the properly calibrated device 10 is inserted forward end 24 first between the layer 120 containing the piece of wood 110 and the layer 122 above it. The probe 14 is inserted into the stack 112 until the sensor 18 in the probe 14 is over the piece of wood 110. The depth indicia 86 are used to judge the distance the probe 14 is inserted into the stack.

Once the sensor 18 is positioned over the piece of wood 110, the cam levers 20, 21 are extended by sliding the slide handle rearward. This pivots the cam levers 20, 21 upward toward the layer 122 above the piece of wood 110. As the cam levers 20, 21 continue to pivot upward, they push against the layer 122 thereby pressing the probe 14 and the sensor 18 against the piece of wood 110. It is in this position that the device 10 makes the most accurate measurement of the wood's moisture content.

After positioning, the meter 16 is activated by pushing the actuation button 98. The user reads the moisture content percentage of the wood by noting the deflection of the needle across the dial 94.

Having described and illustrated the principles of my invention with relation to a preferred embodiment, it will be recognized that the invention can be modified in arrangement and detail without departing from such principles. For example, various mechanical and fluid actuated mechanisms can be employed to urge the sensor at the end of the probe against the lumber to be tested. Therefore, the invention is not limited to the mechanical mechanism in the specifically described embodiment. To illustrate the breadth of this aspect of the invention, other exemplary mechanisms include the following.

A first exemplary mechanism is one that is gas or fluid operated. In such a mechanism, a balloon-like inflatable bag at the forward end of the probe is expanded to urge the sensor against lumber in a stack. The bag is expanded by operating a handle to push against a diaphragm at the opposite end of the probe. When pushed against using the handle, the diaphragm forces gas or fluid through a tube to fill the bag.

Another exemplary mechanism employs a push or twist rod linkage mechanism operated by a handle. When the rod is operated by a handle, the linkage mechanism forces a lever or the like to protrude outwardly from the forward end of the probe, urging the sensor in the probe against the lumber. A further exemplary mechanism employs a cable linkage similar to those used in bicycle brake systems. Such cable linkages can be employed to extend a lever at the forward end of the probe when operated by pulling a lever at the opposite end of the probe.

Also exemplary of the various mechanisms that can be employed to implement the invention are the various configurations available for an extendable member. For example, the extendable member can be configured as a single-piece cam lever rather than the separate cam levers 20, 21 of the preferred embodiment. Such a single-piece cam lever may comprise a bridge portion which straddles the support block 42 and cam portions shaped similarly to the cams 20, 21. Like the cam levers 20, 21, the single-piece cam lever may be pivotally mounted to the support block 42 and the arms 48, 50 to pivot between a reclined and an extended position. The cam levers 20, 21 of the device 10 are preferred over a single-piece cam lever of this type because the cam levers 20, 21 exhibit a reduced tendency to clog from trapped debris such as pitch and sawdust. Still other configurations of extendable members for the probe 14 are suitable to the present invention. Any wood surface engaging element capable of selective projection from the probe to urge the probe against the lumber being tested may be used.

Accordingly, I claim as my invention all embodiments which come within the scope and spirit of the following claims and equivalents thereto.

I claim:

1. A method of measuring the moisture content of stacked wood using an apparatus having an elongated probe with a sensor and an extendable member at a forward end the method comprising:

inserting the probe between a first and a second layer of stacked wood;

positioning the probe with the sensor over a target area in the second layer;

actuating the extendable member to urge the probe away from the first layer and towards the second layer to thereby place the sensor in close proximity to the second layer; and generating a signal from the sensor representing the moisture content of the second layer in the target area.

2. The method of claim 1 comprising:

visually indicating the moisture content of the second layer in the target area.

3. A probe for urging a moisture sensor toward wood in a stack, comprising:

an elongated probe having a forward end, and an opposite end; and a wood surface engaging element located near the forward end of the probe and selectively movable from a first position toward a second position projecting outwardly from the probe a greater distance than when in the first position, whereby with the probe inserted between a first and a second layer of stacked wood, movement of the engaging element toward the second position pushes the forward end of the probe away from the first layer and towards the second layer to place the sensor in closer proximity to the second layer.

4. The apparatus of claim 3 comprising an actuator for moving the wood surface engaging element between the first and second positions.

5. The apparatus of claim 4 wherein the actuator comprises a sliding handle member having a handle portion located at the opposite end of the probe and an arm portion extending longitudinally along the probe to the forward end of the probe, the arm portion engaging the wood surface engaging element at the forward end of the probe, the sliding handle member being slidable between a first and a second position to move the wood surface engaging element between the first and second positions, respectively.

6. The apparatus of claim 3 in which the engaging element comprises an extendable member movable between a reclined and an extended position.

7. The apparatus of claim 6 wherein the extendable member comprises a cam lever having a hinged end pivotally fastened to the probe and a curved top surface for engaging a layer of stacked wood.

8. The apparatus of claim 7 wherein the extendable member comprises a second cam lever also operable from the opposite end of the probe to move between a reclined and an extended position.

9. The apparatus of claim 6 comprising an actuator for moving the extendable member between the reclined and extended positions.

10. The apparatus of claim 9 wherein the actuator comprises a sliding handle member having a handle portion located at the opposite end of the probe and an arm portion extending longitudinally along the probe to the forward end of the probe, the arm portion engaging the extendable member at the forward end of the probe, the sliding handle member being slidable between a first and a second position to move the extendable member between the first and second positions, respectively.

11. The apparatus of claim 10 wherein the extendable member comprises a cam lever having a hinged end pivotally fastened to the probe and a curved top surface for engaging a layer of stacked wood.

12. The apparatus of claim 11 wherein the extendable member comprises a second cam lever also engaged by the arm portion of the sliding handle member, the sliding handle member moving the cam levers jointly between reclined and extended positions.

13. The apparatus of claim 10 wherein the probe comprises first and second cover plates, and the arm portion of sliding handle member is of a reduced dimension adjacent to the extendable member so as to avoid binding with the cover plates when the arm is slid to move the extendable member.

14. The apparatus of claim 13 in which at least one of the cover plates has an exposed outer surface with visual depth insertion indicia thereon.

15. The apparatus of claim 3 comprising indicia marked on the probe for indicating the depth of insertion of the sensor into a gap in a stack of wood.

16. The apparatus of claim 3 in which the probe includes first and second cover plates at least one of which has an interior surface of an electrically conductive material, the sensor being formed from a portion of the electrically conductive interior surface.

17. The apparatus of claim 3 comprising a meter electrically connected to the sensor to receive an electrical signal related to the moisture content of the stacked wood from the sensor, the meter being operative to indicate the moisture content of the stacked wood.

18. The apparatus of claim 17 wherein the meter is mounted to the probe at the opposite end.

19. A method of measuring the moisture content of stacked wood using a probe having an elongated body and an extendable member, the method comprising:

inserting the probe between a first and a second layer of stacked wood; and moving the extendable member relative to the body of the probe and against wood of the first layer to urge the body away from the first layer and towards the second layer.

* * * * *